United States Patent
Kang et al.

(10) Patent No.: US 12,017,087 B1
(45) Date of Patent: Jun. 25, 2024

(54) LED INFRARED IRRADIATOR

(71) Applicants: BIOSYN KOREA CO., LTD., Gwangju (KR); BOJONG GLOBAL HEALTH CARE CO., LTD., Gwangju (KR); BOJONG MC CO., LTD., Gyeonggi-do (KR)

(72) Inventors: Jong Ok Kang, Gyeonggi-do (KR); Jung Soo Lim, Gyeonggi-do (KR)

(73) Assignees: BIOSYN KOREA CO., LTD., Gwangju (KR); BOJONG GLOBAL HEALTH CARE CO., LTD., Gwangju (KR); BOJONG MC CO., LTD., Gyeonggi-Do (KR)

( * ) Notice: Subject to any disclaimer, the term of this patent is extended or adjusted under 35 U.S.C. 154(b) by 0 days.

(21) Appl. No.: 18/512,342

(22) Filed: Nov. 17, 2023

(30) Foreign Application Priority Data

May 12, 2023 (KR) .................. 10-2023-0061460

(51) Int. Cl.
*A61N 5/06* (2006.01)

(52) U.S. Cl.
CPC .... *A61N 5/0625* (2013.01); *A61N 2005/0626* (2013.01); *A61N 2005/0632* (2013.01); *A61N 2005/0638* (2013.01); *A61N 2005/0643* (2013.01); *A61N 2005/0652* (2013.01); *A61N 2005/066* (2013.01); *A61N 2005/0664* (2013.01)

(58) Field of Classification Search
CPC .......... A61N 5/0625; A61N 2005/0626; A61N 2005/0632; A61N 2005/0638; A61N 2005/0643; A61N 2005/0652; A61N 2005/066; A61N 2005/0664
See application file for complete search history.

(56) References Cited

U.S. PATENT DOCUMENTS

| | | | |
|---|---|---|---|
| 2019/0247254 A1* | 8/2019 | Naber | A61G 7/1046 |
| 2020/0008996 A1* | 1/2020 | Zack | A61H 33/14 |
| 2021/0100378 A1* | 4/2021 | Youngblood | A61F 7/007 |
| 2022/0039325 A1* | 2/2022 | Adams | F21V 17/002 |
| 2022/0257461 A1* | 8/2022 | Schlender | A61H 1/005 |

FOREIGN PATENT DOCUMENTS

| | | | | |
|---|---|---|---|---|
| CN | 108924976 A | * | 11/2018 | .......... H05B 1/0272 |
| JP | 2007195741 A | * | 8/2007 | |
| JP | 7093606 B1 | * | 6/2022 | |
| KR | 1020060030155 | | 4/2006 | |
| KR | 101433070 B1 | * | 8/2014 | |
| KR | 101588369 | | 1/2016 | |
| KR | 101588369 B1 | * | 1/2016 | |
| KR | 102431396 | | 8/2022 | |

\* cited by examiner

*Primary Examiner* — Carl H Layno
*Assistant Examiner* — Aya Ziad Bakkar
(74) *Attorney, Agent, or Firm* — IPLA P.A.

(57) ABSTRACT

An LED infrared irradiator includes an upper plate, a lower plate having a space for the user to lie down, a PC board disposed on the upper surface of the lower plate and having a size that can accommodate the entire body of the user, a handle part, a head part, a cover part, an oxygen generator, and a control unit attached to the upper side of the upper plate, wherein the power source of the lower plate consists of a chamber power source unit, a lower plate LED power source unit and a far-infrared heating element, and the power source of the upper plate consists of a upper plate LED power source, a upper plate UVC LED power source.

15 Claims, 14 Drawing Sheets

LED INFRARED IRRADIATOR

BACKGROUND

The present invention relates to an LED infrared irradiator. More specifically, the present invention relates to an LED infrared irradiator that can prevent various kinds of diseases and pains by increasing the core body temperature of a treatment subject (user).

The human body is greatly influenced by the core body temperature. Even if the core body temperature increases or decreases by just 0.5° C. to 1° C., the activities that release, convert, and store energy are affected.

It is known that when the core body temperature rises by 1° C., the basal metabolic rate increases by 15%. Conversely, when body temperature drops, blood circulation does not work properly, and oxygen, nutrients and immune substances carried by blood are not properly transported throughout the body, which breaks the balance in the body and makes it easy to be exposed to various diseases. Likewise, the core body temperature plays an important role in regulating our body's temperature and thus increasing immunity.

In general, infrared light has the property that it is easily reflected if the wavelength is short, whereas if the wavelength is long, the infrared light is easily absorbed when it reaches an object, and therefore, the infrared light has strong penetrating power and the human body feels warm when exposed to the infrared light. When a person sits in the sun, the person can feel hot because the infrared ray contained in the sun penetrate deep into the skin and create heat.

The infrared rays can be broadly divided into near infrared rays, mid infrared rays, and far infrared rays. Among them, near-infrared rays are lights between 780 nm and 1200 nm and are located between the visible light rays and the mid-infrared rays.

The visible light rays are the lights that can be seen with the eyes, and their wavelengths are 380 nm to 780 nm. The near-infrared rays have wavelengths close to red visible light rays in electromagnetic waves with wavelengths of 780 nm to 2,500 nm and their properties are close to those of the visible light rays and are called "invisible light" and are used in infrared cameras. The near-infrared rays are applied to infrared cameras, infrared communications, and remote controls for home appliances.

The near-infrared rays have much shorter wavelengths than that of the far-infrared rays, and their penetration power is more than 10 times deeper than that of the far-infrared rays. The characteristic of near-infrared rays is that they are short-wavelength light rays closest to solar heat with a heating element temperature of 1,800° C. to 2,200° C. As a light source that generates light, a light emitting diode (hereinafter referred to as "LED") has many advantages such as high luminous efficiency, long lifespan and eco-friendliness. Today, the number of technological fields using LEDs continues to increase.

Korean Patent Registration No. 10-1942547 discloses a "whole body therapy device using LED" (hereinafter referred to as "prior art") as shown in FIG. 1 as the prior art.

The conventional art shown in FIG. 1 includes a body part 1 including an upper plate on which a user is positioned, a cover part 5 coupled to the body part 1 and covering the upper plate, and a first light irradiation unit 6 disposed in the body part 1 and irradiating lights from the lower side of the upper plate toward the upper plate, and a second light irradiation unit 2 disposed inside the cover part 5 and irradiating lights toward the upper plate.

The first light irradiation unit 6 and the second light irradiation unit 2 include a plurality of bar-shaped light modules in which a plurality of light sources are arranged in a row. Further, there are disposed that a ventilation device 8 for discharging heat generated from the first light irradiation unit 6 and the second light scanning unit 2 to the outside, a side plate (7) installed on the upper part of one side of the body unit (1), and an infrared ray lamp for keeping the user's feets warm.

The conventional art has a problem in that it cannot expect beneficial therapeutic effects on the human body because it does not use near-infrared ray LEDs. The light irradiator according to the conventional art is an irradiation device that uses a specific wavelength band of a light source, and irradiates the skin with light generated from a light source that generates a certain wavelength having a healing effect on the human body. Therefore, the irradiation device is used for skin treatments such as activating skin cells, alleviating wrinkles, removing acne and alleviating atopy phenomenon without side effects regardless of any skin type or race The light irradiator using this LED light source includes a fixed light therapy device used in hospitals and skin care shops, a portable light therapy devices used at home and so on. Recently, Recently, as various light treatment effects have been confirmed and interest in skin care has increased, various research and developments have been conducted on light irradiators for skin treatment.

SUMMARY OF THE INVENTION ntion is to provide an LED infrared ray irradiator that intensively increases the user's core body temperature with near-infrared ray wavelengths that penetrate deep into the human skin and increase the temperature.

A LED infrared irradiator of the present invention comprises an upper plate, a lower plate having a space for the user to lie down, a PC board disposed on the upper surface of the lower plate and having a size that can accommodate the entire body of the user, a handle part, a head part, a cover part, an oxygen generator, and a control unit attached to the upper side of the upper plate, wherein the power source of the lower plate consists of a chamber power source unit, a lower plate LED power source unit and a far-infrared heating element, and the power source of the upper plate consists of a upper plate LED power source, a upper plate UVC LED power source, and a far-infrared heating element, and wherein the material of the upper and lower plates is ABS resin, and the upper and lower plates consist of double walls being characterized in that an eco-friendly foamed graphite insulation material is built in the middle of the wall between the upper and lower plates; the lower plate includes a bracket 21, a lower body part 22, a pillow 23 for placing the user's head, a storage stand 24 for placing a water cup, etc., a mobile phone storage stand 25, a shock absorber 26, and a sweat outlet 27, a hinge 28, a moving wheel 31, and a space 29 into which the injection line that supplies the fluid can enter when the user receives an IV injection; the control unit includes a power unit 110, an operating mode control unit 120, a sensor unit 130, a timer unit 140, an alarm sound generator 150, a chamber opening/closing unit 160, a display driving unit 170, and a ventilation unit 180, an information processing unit 190 and a memory unit 200; the power source unit 110 includes a chamber power source unit 112, a lower plate LED power source unit 113, an upper plate LED power source unit 114, an upper plate UVC LED power source unit 115, and a far-infrared heating element 116; and the sensor unit 130 includes a temperature sensor 131, a humidity sensor 132, and a human body detection sensor 133 for detecting whether a user is inside the chamber.

Further, in the LED infrared irradiator of the present invention, the lower LED power source unit 113 consists of an A-type LED unit 52 in which several 600 nm visible light LEDs are arranged, and a B-type LED unit 53 in which 810 nm LEDs, 940 nm LEDs, and 1,200 nm LEDs are mixed and arranged; wherein the number of A-type LED units 52 is 5 to 10, and the number of B-type LED units 53 is 5 to 10; and wherein the lower plate LED power source unit 113 converts AC 120-220V into 12V direct current using the AC/DC converter 51 and supplies it, and controls the power of the A-type LED unit and the B-type LED unit, respectively.

Further, in the LED infrared irradiator of the present invention, the upper plate LED power source unit 114 consists of an A-type LED unit 52 in which several 600 nm visible light LEDs are arranged, a B-type LED unit in which 810 nm LEDs, 940 nm LEDs and 1,200 nm LEDs are mixed and arranged 53 and an ultraviolet UVC LED 54; the number of the A-type LED units 52 is 4 to 8, the number of the B-type LED units 53 is 4 to 8, and the number of the ultraviolet UVC LEDs (54) is 2 to 3; and the lower plate LED power source unit 113 converts AC 120/220V into 12V direct current using the AC/DC converter 51 to supply power to the A-type LED unit and B-type LED unit, respectively; and converts AC 120/220V into 48V direct current using an AC/DC converter 51, supplies it to two ultraviolet LEDs 54 and controls them respectively.

Further, in the LED infrared irradiator of the present invention, the shock absorber 26 includes an actuator 300 of which the upper part is coupled to the first fixing part 310 attached to the upper plate 10, and of which the lower plate is coupled to the second fixing part 320 attached to the lower plate 20; and one or more hinges 330 for combining the upper plate 10 and the lower plate 20 and supporting the upper plate so that it can move up and down.

According to the present invention, there is an effect that the near-infrared ray penetrates deep into the human body's skin and warms the skin while increasing the core body temperature, and convective heat generated from multiple LEDs is effectively block, allowing users to receive infrared ray irradiation all over their body in a comfortable environment.

Further, according to the present invention, near-infrared rays emitted from LED promote the production of nitric oxide (NO) and have effects on blood circulation, pain relief, waste removal and sterilization.

DETAILED DESCRIPTION OF THE INVENTION

Hereinafter, the present invention will be described in detail with reference to the drawings.

Figure 1:
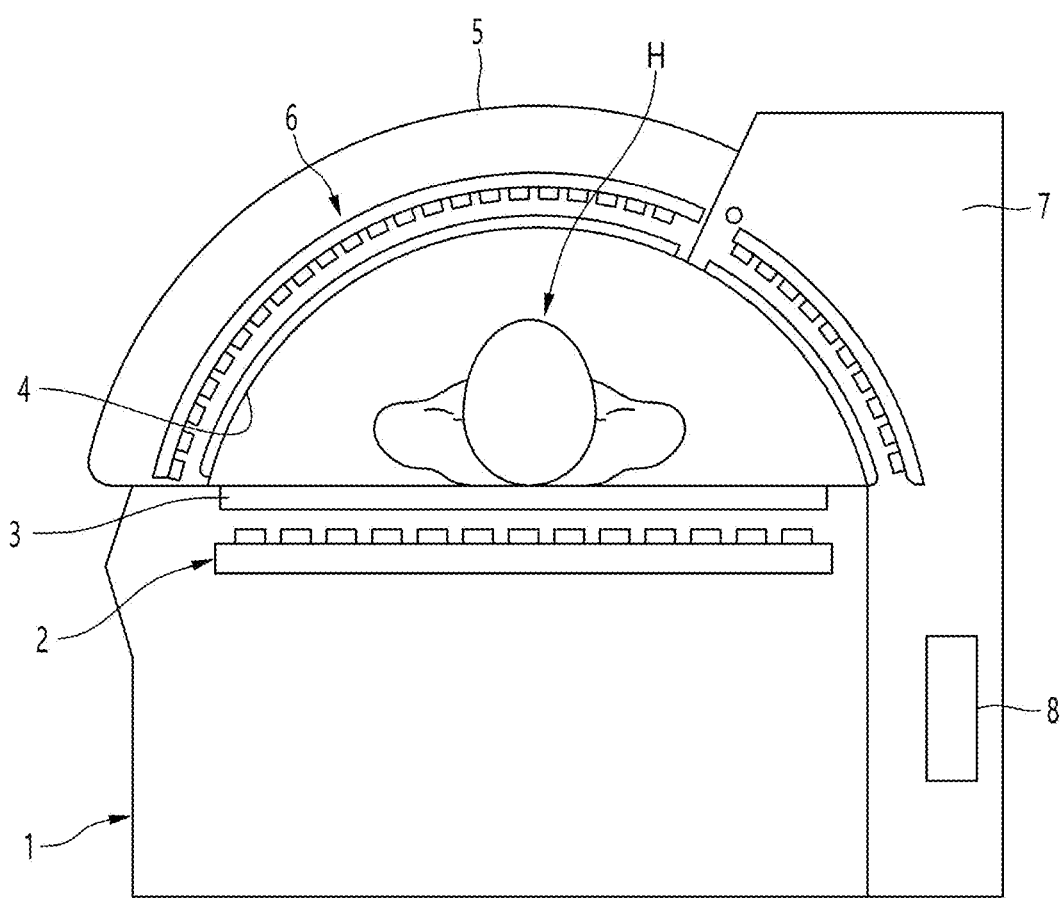
FIG. 1 is a perspective view of a conventional LED infrared ray irradiator.
Figure 2:
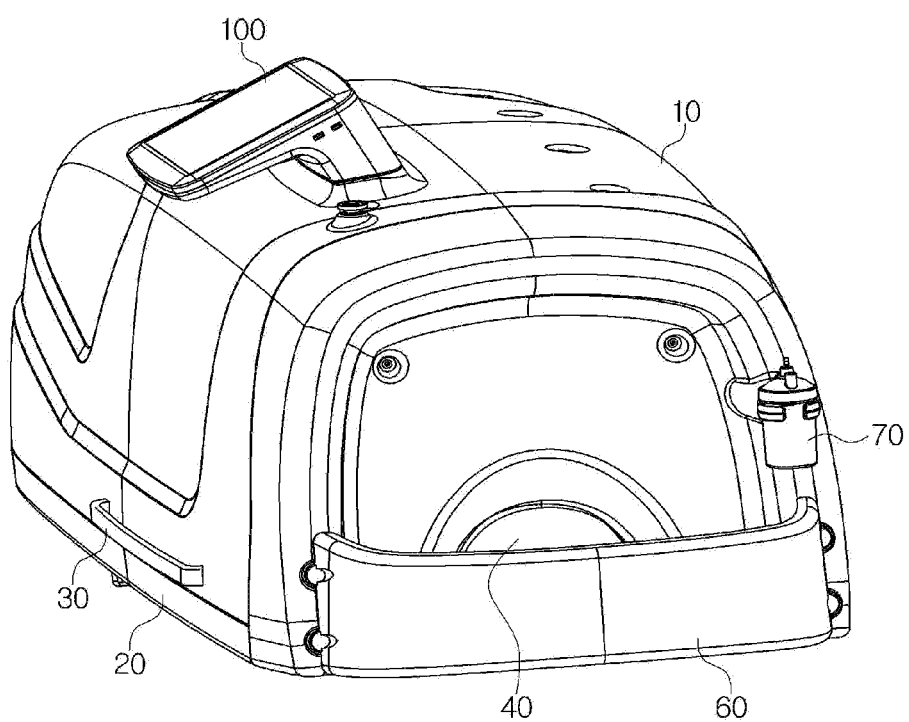
FIG. 2 is a perspective view of a whole body thermotherapy device according to an embodiment of the present invention.
Figure 3:
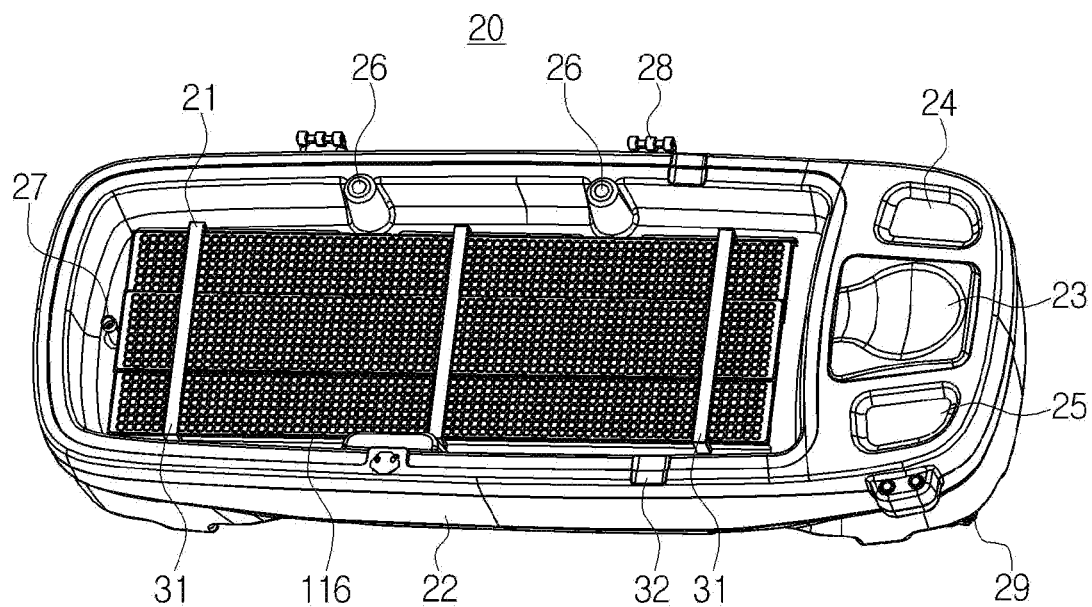
FIG. 3 is a configuration diagram of a lower plate according to an embodiment of the present invention.
Figure 4:
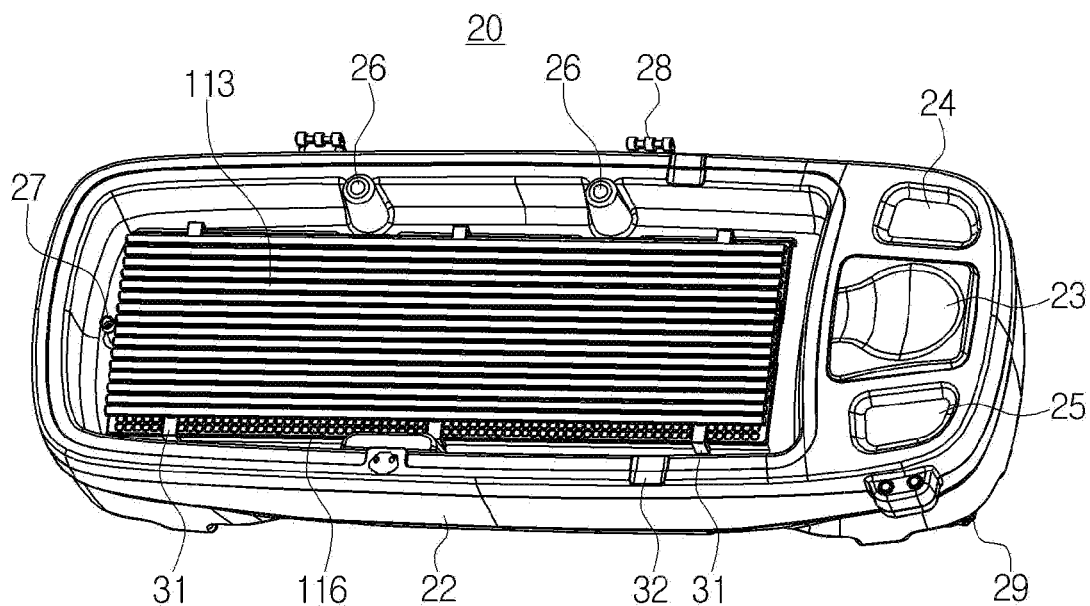
FIG. 4 is a configuration diagram of a LED power source on the lower plate according to an embodiment of the present invention.
Figure 5:
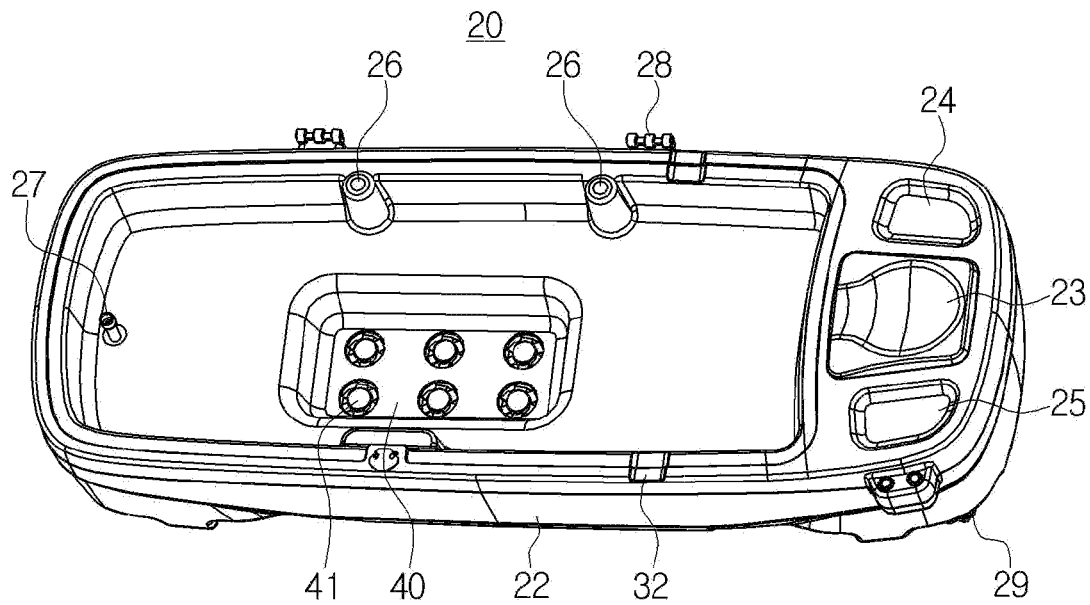
FIG. 5 is a view with a heater bracket on the lower plate removed according to an embodiment of the present invention.

FIG. 2 is a perspective view of a whole body thermotherapy device according to an embodiment of the present invention, FIG. 3 is a configuration diagram of the lower plate according to an embodiment of the present invention, and FIG. 4 is a configuration diagram of a LED power source on the lower plate according to an embodiment of the present invention. FIG. 5 is a view with a heater bracket on the lower plate removed according to an embodiment of the present invention.

Figure 6:
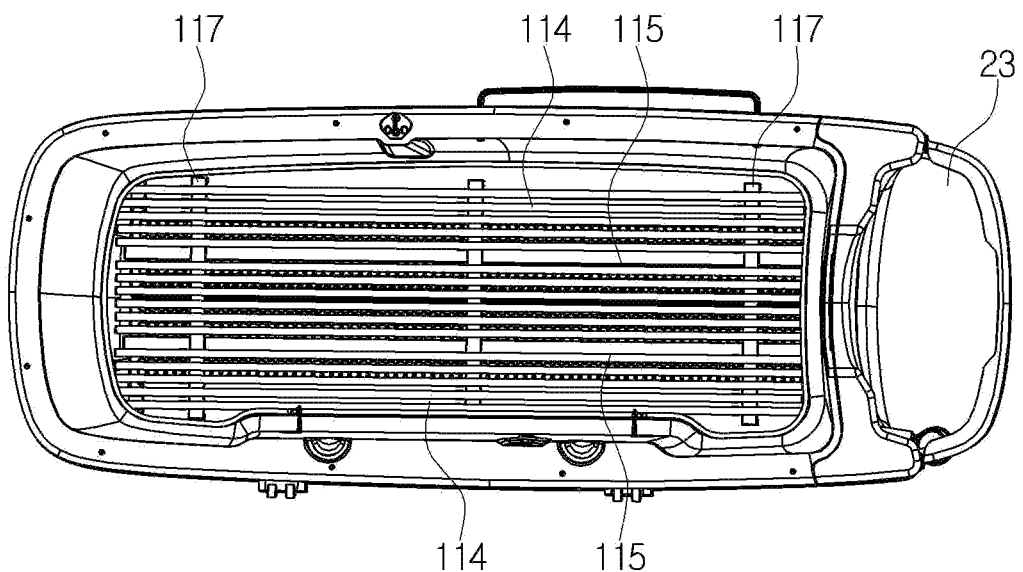
FIG. 6 is a configuration diagram of an upper part according to an embodiment of the present invention.
Figure 7:
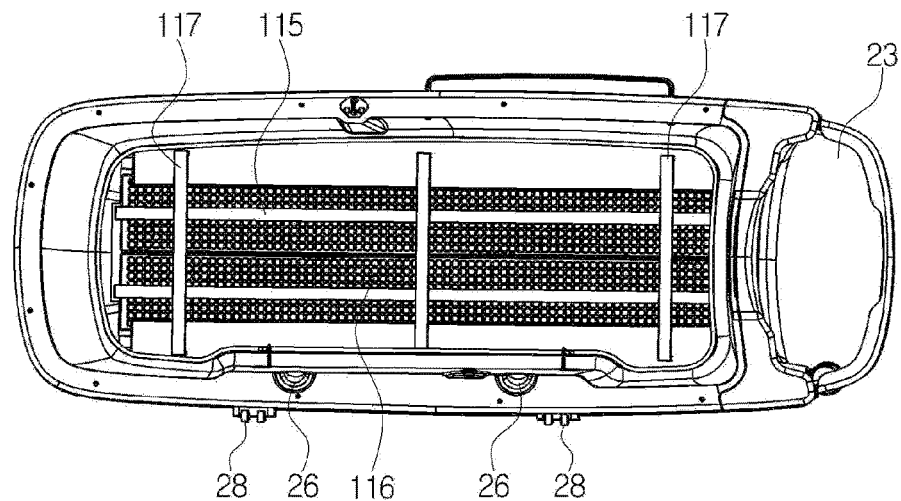
FIG. 7 is a configuration diagram of a far-infrared ray heating element disposed on an upper plate according to an embodiment of the present invention.
Figure 8:
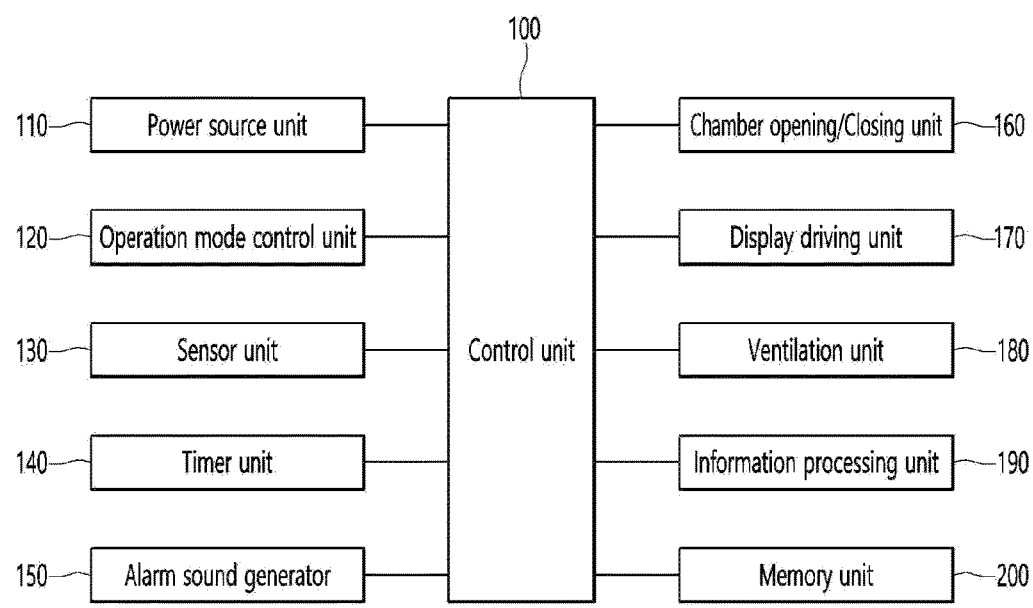
FIG. 8 is a block diagram of a control unit according to an embodiment of the present invention.
Figure 9:
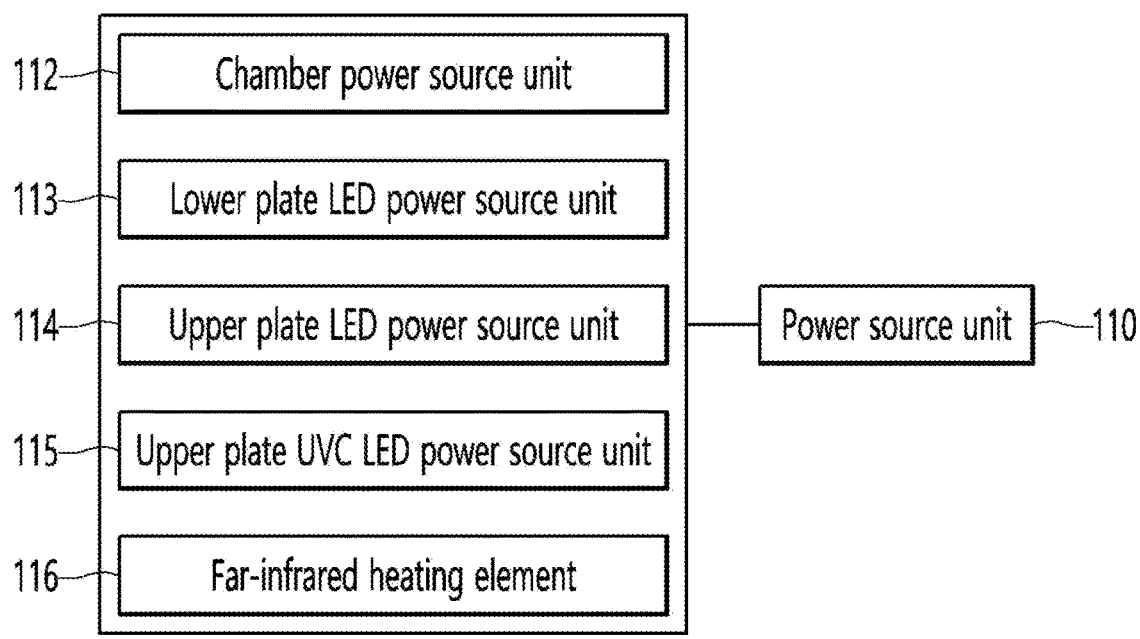
FIG. 9 is a configuration diagram of a power source according to an embodiment of the present invention.
Figure 10:
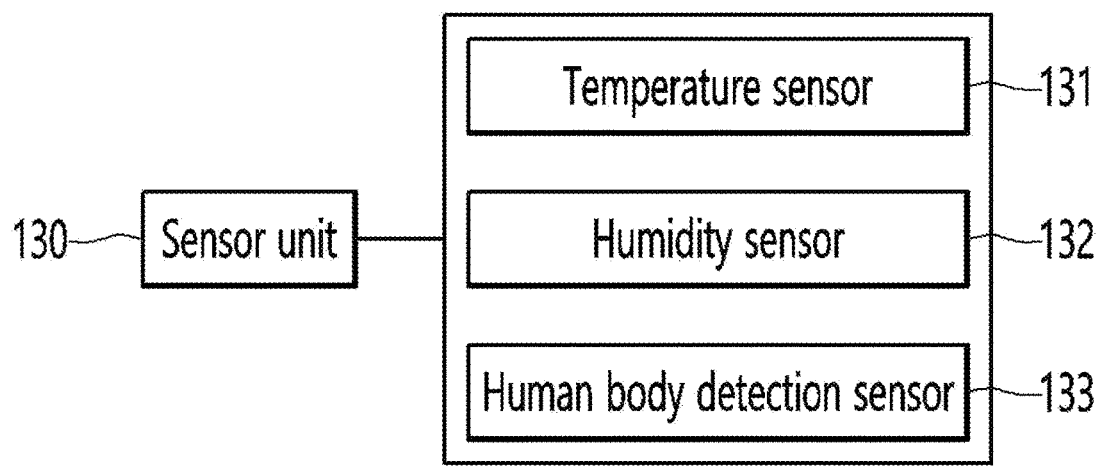
FIG. 10 is a configuration diagram of a sensor unit according to an embodiment of the present invention.
Figure 11:
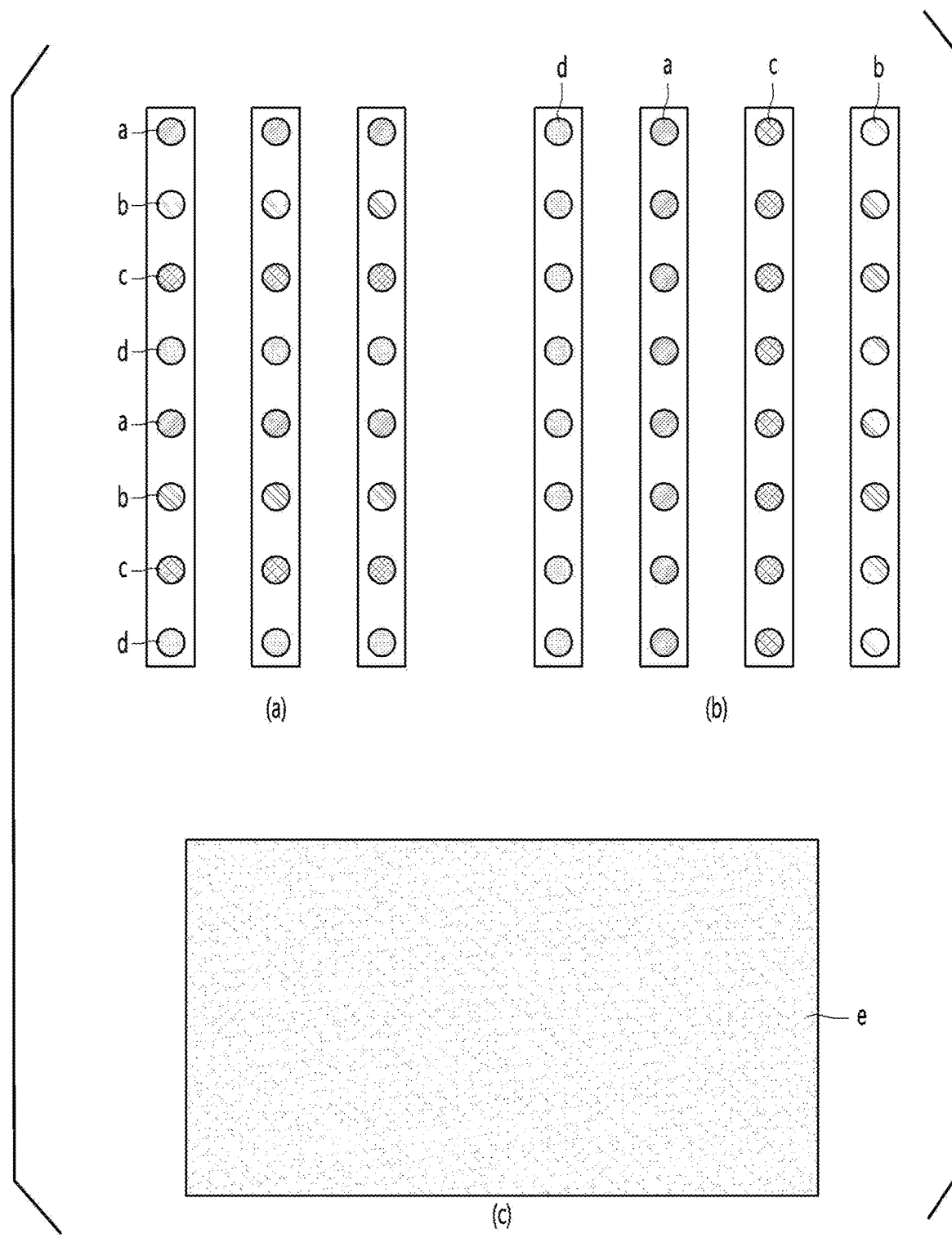
FIG. 11 is a configuration diagram of an LED unit according to an embodiment of the present invention.
Figure 12:
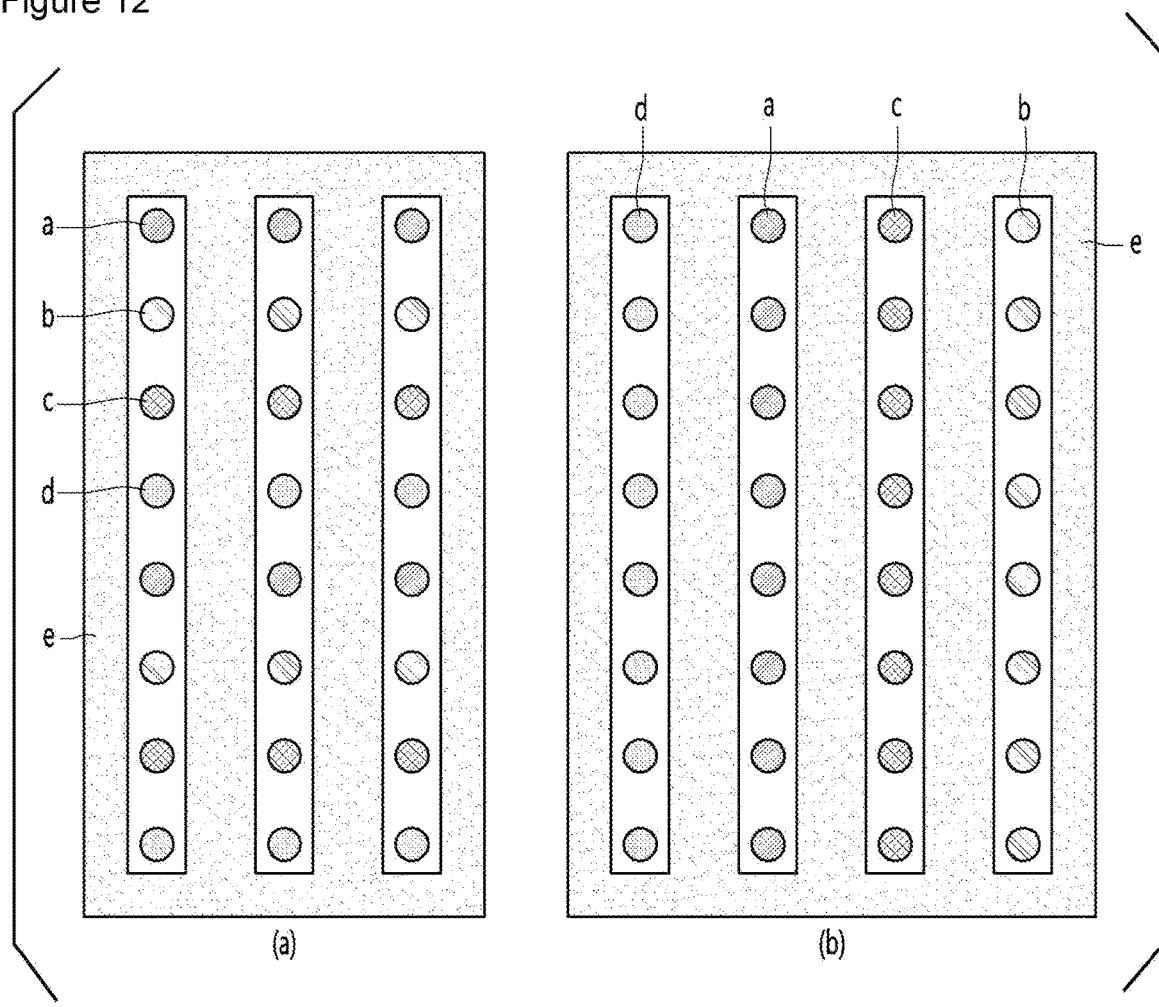
FIG. 12 is a diagram with multiple wavelength LEDs combined.
Figure 13:
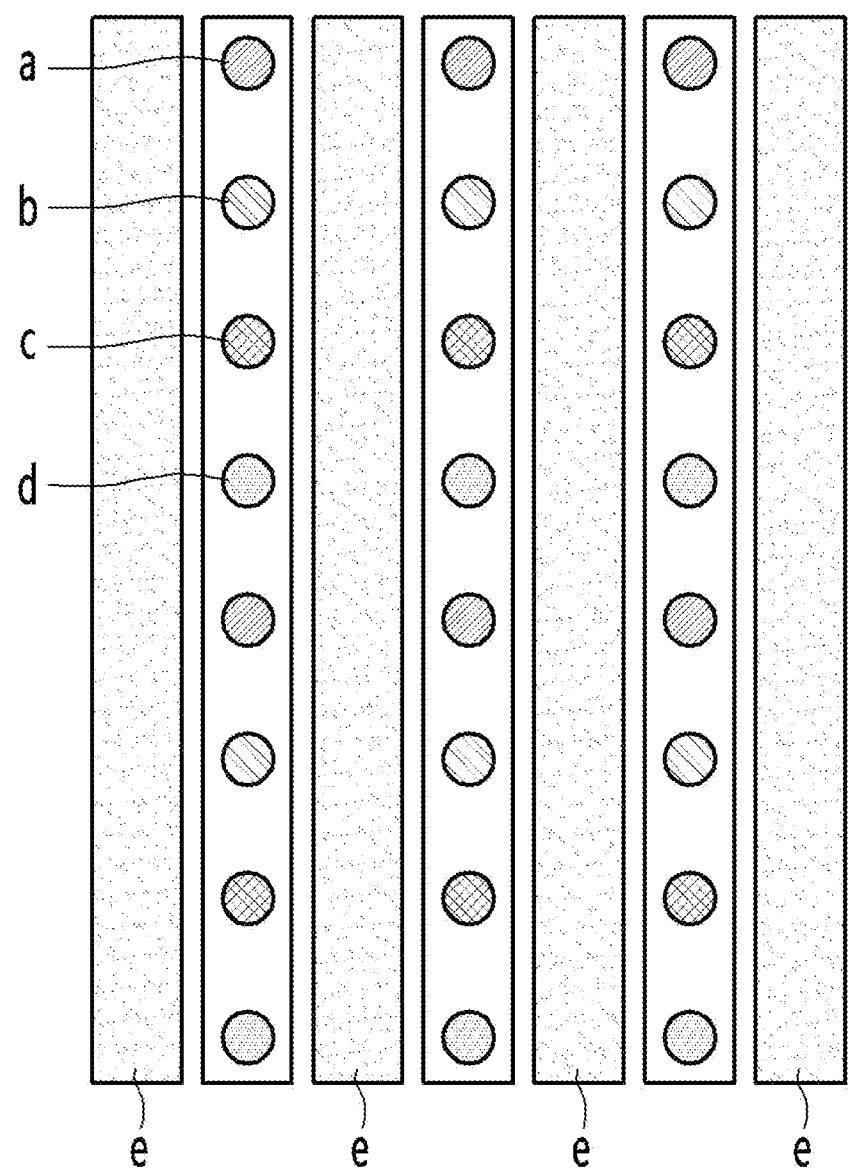
FIG. 13 is a diagram with a near-infrared ray LED and a far-infrared ray heating element combined.
Figure 14:
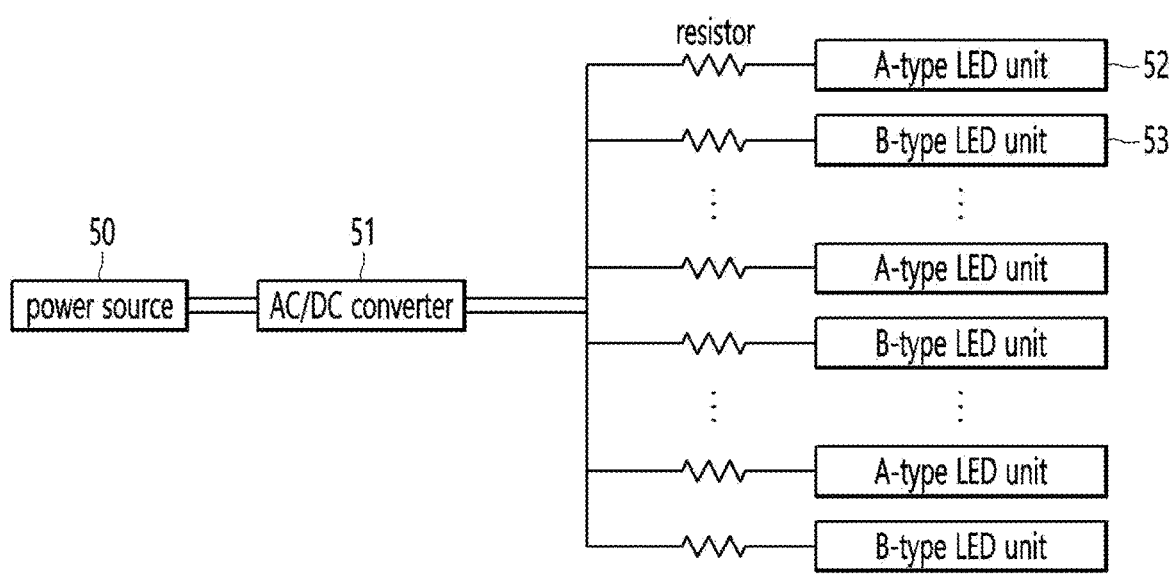
FIG. 14 is a configuration diagram of a LED power source unit on the lower plate.
Figure 15:
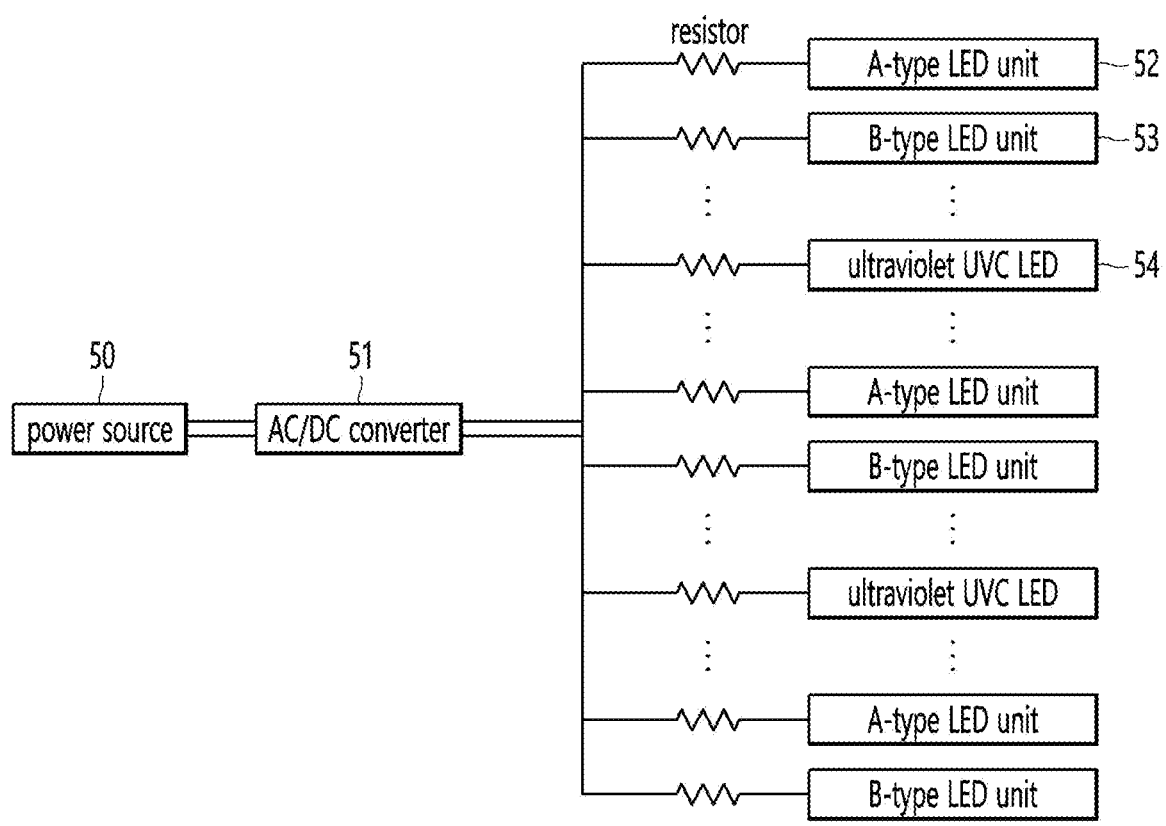
FIG. 15 is a configuration diagram of a LED power source unit on the upper plate.
Figure 16:
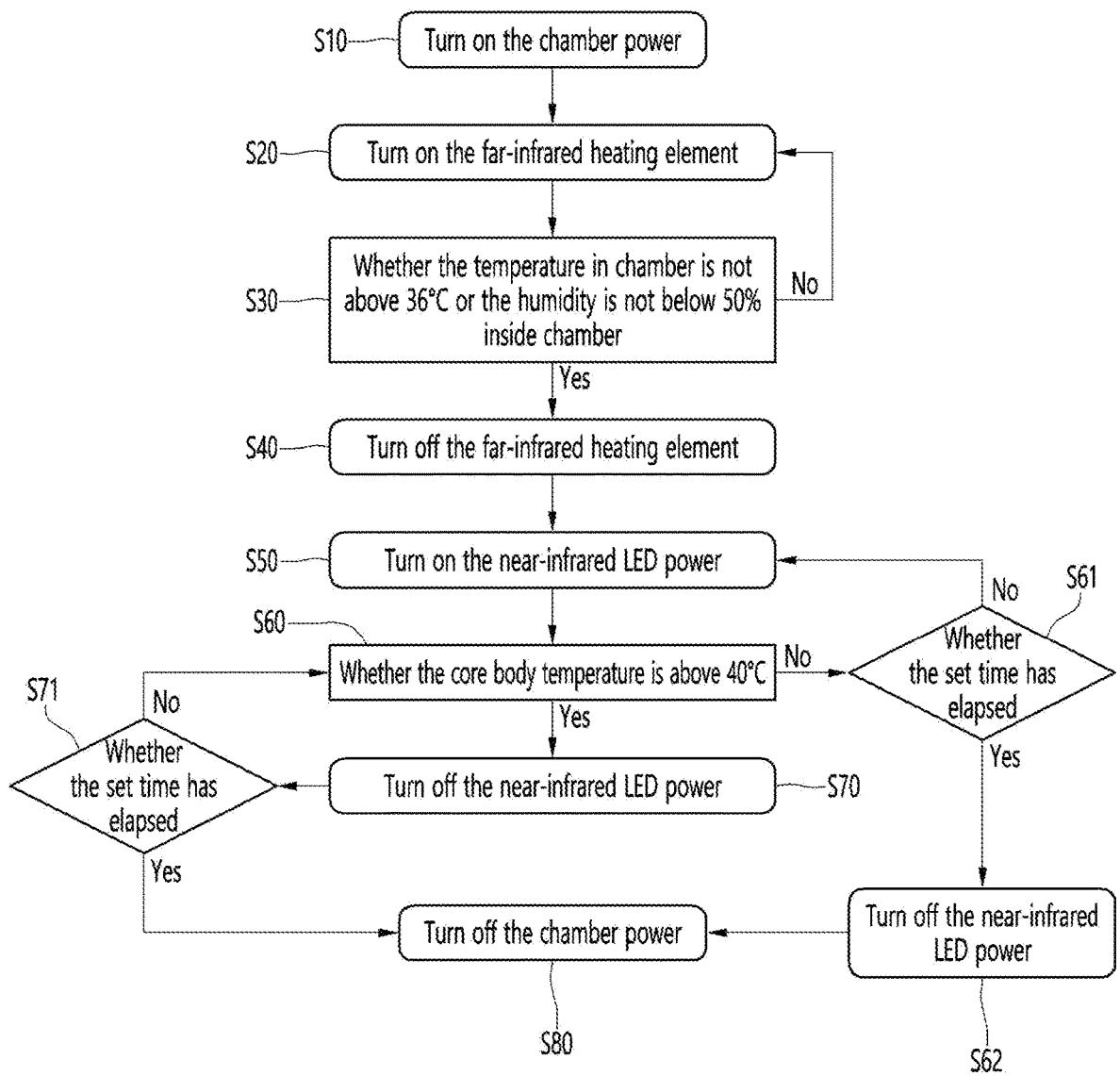
FIG. 16 is a flow chart showing the operation of the LED infrared ray irradiator of the present invention.
Figure 17:
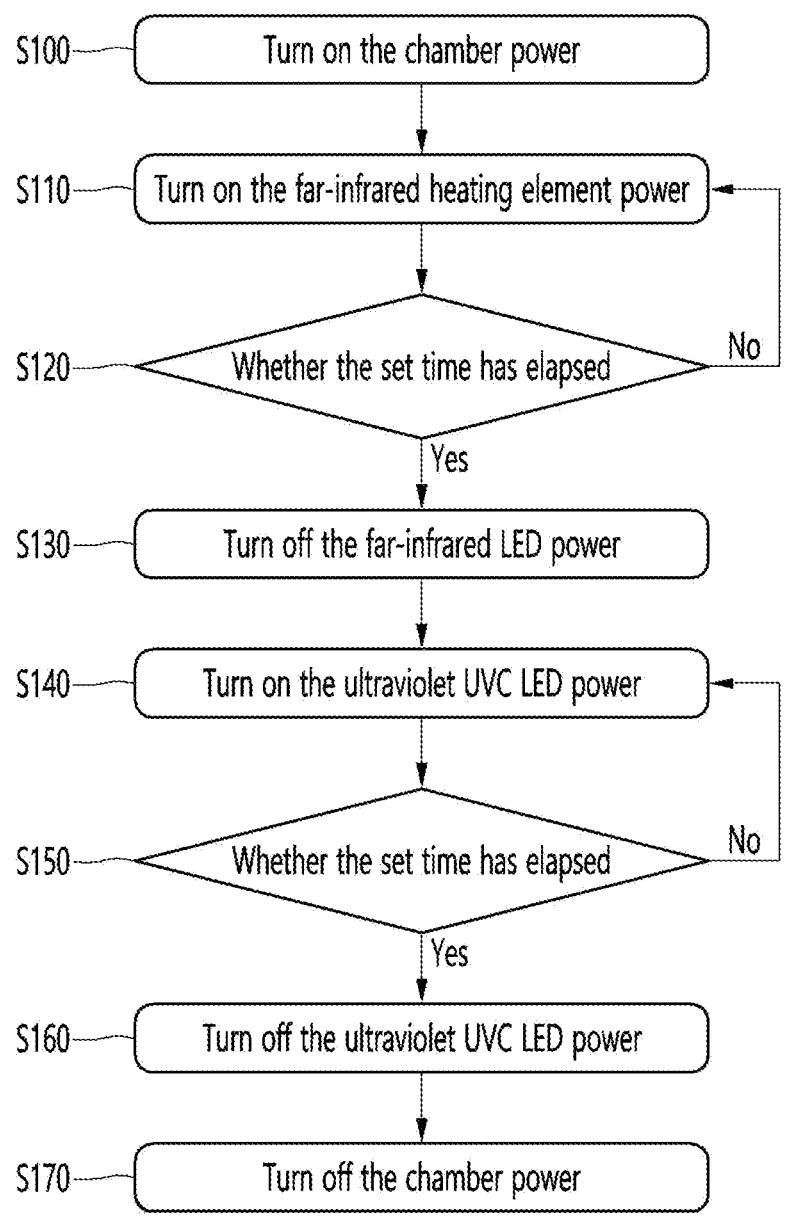
FIG. 17 is a flow chart showing a disinfection method in the chamber of the present invention.
Figure 18:
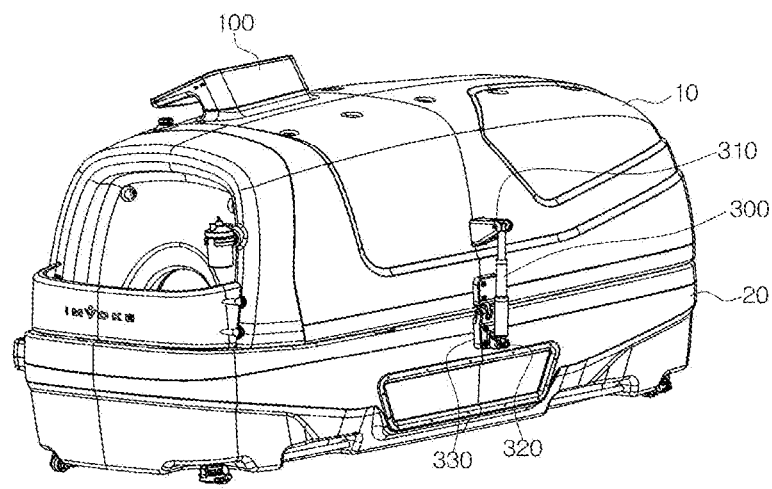
FIG. 18 is a structural diagram of an actuator installed on the upper plate.
Figure 19:
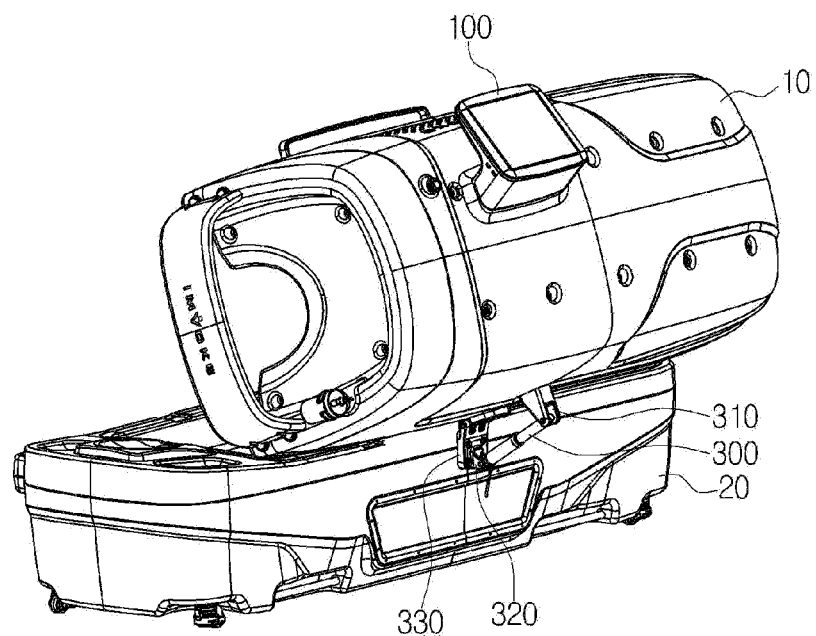
FIG. 19 is a diagram showing that the upper plate opens by the operation of the actuator.

FIG. 6 is a configuration diagram of an upper part according to an embodiment of the present invention, and FIG. 7 is a configuration diagram of a far-infrared ray heating element disposed on an upper plate according to an embodiment of the present invention. FIG. 8 is a block diagram of a control unit according to an embodiment of the present invention, FIG. 9 is a configuration diagram of a power source according to an embodiment of the present invention, and FIG. 10 is a configuration diagram of a sensor unit according to an embodiment of the present invention. FIG. 11 is a configuration diagram of an LED unit according to an embodiment of the present invention, FIG. 12 is a diagram with multiple wavelength LEDs combined, and FIG. 13 is a diagram with a near-infrared ray LED and a far-infrared ray heating element combined. FIG. 14 is a configuration diagram of a LED power source unit on the lower plate, and FIG. 15 is a configuration diagram of a LED power source unit on the upper plate. FIG. 16 is a flow chart showing the operation of the LED infrared ray irradiator of the present invention, and FIG. 17 is a flow chart showing a disinfection method in the chamber of the present invention. FIG. 18 is a structural diagram of an actuator installed on the upper plate, and FIG. 19 is a diagram showing that the upper plate opens by the operation of the actuator.

Types of Infrared Rays

Infrared rays are divided into near infrared rays, mid infrared rays and far infrared rays depending on the wavelength.

The human skin consists of stratum corneum, epidermis, dermis, subcutaneous fat and muscle. A depth of 4 mm or more from the skin is called subcutaneous fat, and the thickness of the subcutaneous fat is about 2 mm.

In the present invention, the user's core body temperature can be increased by elevating the temperature most effectively and in a short time through heating of the subcutaneous fat layer.

The near-infrared wavelength of 700 nm to 1,200 nm used in the present invention can penetrate more than 5 mm deep into the skin and heat the human body.

The near-infrared wavelength is a direct heat transfer method that does not require separate preheating time as the light energy instantaneously generates 2,200° C. within 10 seconds rather than the existing thermal convection method, delivering heat energy with a thermal efficiency of over 90%.

The world-famous scientific journal Nature published in 2006 that near-infrared rays have been shown to have over 1,000 effects in plant growth and human treatment experiments conducted by NASA (National Aeronautics and Space Administration) for a long time. In a published NASA paper, it was claimed that among the lights coming from the sun, only near-infrared rays have cell activation and biological healing effects, so they are the light of life that cures all diseases even though it is not applied or eaten. Since then, as a result of research by many medical institutions and scientists, the range of near-infrared rays has been discovered to have numerous different efficacies in each region within the range of 700 nm to 1,200 nm, and has been called the miracle light. It is also called a miraculous light because there are no side effects no matter how much it is used.

For a tumor such as cancer, the wavelength needs to be adjusted to achieve the deepest penetration. The optimal near-infrared region that penetrates more than 5 mm into the skin is 850 nm or 1,200 nm. The wavelengths between these two regions most efficiently penetrate deep into the skin and increase the body's core temperature. Therefore, in one embodiment of the present invention, the near-infrared region generated from the LED and the wavelength of 700 nm to 1, 200 nm in the skin depth region of 5 mm or more are used.

FIG. 2 is a perspective view of a whole body thermotherapy device according to an embodiment of the present invention.

The term "chamber" used in the present invention is defined as a cylindrical container with a space for near-infrared treatment. The chamber consists of an upper plate and a lower plate.

When the chamber opening/closing part turns "ON", the upper chamber opens upward, and when "OFF", the upper chamber closes downward. For convenience of explanation, the upper chamber is referred to as the "upper plate" and the lower chamber is referred to as the "lower plate."

A person to be treated with the LED infrared irradiator of the present invention is defined as the "user."

One side of the chamber of the present invention is open, the user lies down on a poly carbonate (PC) board of the lower plate, and the user's head is located outside the lower plate.

EMBODIMENTS

The LED infrared irradiator of the present invention shown in FIG. 2 includes an upper plate 10 and a lower plate 20. It consists of a handle part 30, a head part 40, a cover part 60, an oxygen generator 70, and a control unit 100.

A control unit 100 is provided at the upper side of the upper plate 20. The control unit 100 controls components mounted on the upper plate 10 and the lower plate 20. The control unit 100 is a 12.1-inch touch plate as a display.

A manager can hold the handle part 30 and open the upper plate 10. Alternatively, the upper plate 20 can be opened and closed when the manager operates a chamber opening and closing unit 160 of the control unit 100.

The cover part 16 covers the head part 40 so that the user's head is not visible.

The material of the upper and lower plates of the chamber is ABS resin and is composed of double layers. An eco-friendly insulation material is built in between the double-layered upper and lower plates.

The insulation material used in one embodiment of the present invention is an eco-friendly fermented graphite pad. More specifically, it is an eco-friendly insulation material that does not use a freon gas, etc.

In another embodiment of the invention, the insulation material is a foam plastic series, and extruded polystyrene (XPS), foam styrene (EPS), foam polypropylene (EPP) and foam polyethylene (EPE) can be selectively used.

The temperature in the chamber is 80° C. The ABS resin is a synthetic resin that can withstand heat up to 250° C.

The eco-friendly insulating material blocks the heat generated by the rise of temperature in the upper and lower plates due to internal heat generation.

The oxygen generator 70 is attached to the upper part of the head part 40 on one side of the upper plate 10. If the user needs oxygen supply, a hose is immediately connected to the user's nose and oxygen is supplied.

FIG. 3 is a configuration diagram of the lower plate according to an embodiment of the present invention.

The lower plate 20 consists of a bracket 21, a lower body part 22, a pillow 23 for placing the user's head, a storage stand 24 for placing a water cup, etc., a mobile phone storage stand 25, a shock absorber 26, a sweat outlet 27, a hinge 28, a moving wheel 29, and an injection line 29 that supplies fluid when the user receives an IV injection.

A PC board made of transparent plastic is provided on the lower plate 20 to allow light to pass through it. The user lies down on the PC board (not shown).

The material of the pillow 23 is soft medical silicone.

In one embodiment of the present invention, the upper plate and the lower plate 20 are coupled with two hinges 28. The means for opening and closing the upper plate 10 is a shock absorber 26.

The shock absorber 26 includes an air pressure shock absorber, a hydraulic shock absorber, or an actuator. The shock absorber 26 can have two hydraulic shock absorbers installed inside the lower plate 20 as shown in FIGS. 3, 4, and 5.

In another embodiment of the present invention, the actuator is installed outside the upper plate 10.

The upper plate 10 can be opened and closed using the actuator 300 shown in FIGS. 18 and 19. When the actuator 300 is used, there is no noise and it is safe.

In an embodiment of the present invention, the far-infrared heating element 116 uses an illite heating element with good heat generation efficiency. The illite radiates a far-infrared ray energy having the same wavelength as that of the human body. Illite mined in Yeongdong, Chungcheongbuk-do, republic of Korea is a representative clay mineral, and contains porous (low in potassium) biotite-based minerals and has a plate-like structure.

The Illite heating element has superior elasticity and adsorption compared to other minerals. It is said that even if the same amount of heat is applied, the heat being generated by illite inside the core body is much greater than the heat generated by other minerals.

According to research reports, it is said that the far-infrared rays emitted from illite can improve blood circulation, activate cells, strengthen immunity, provide deep penetration heat into core body, antibacterial and deodorize, and reduce cancer cell proliferation.

FIG. 4 is a configuration diagram of the lower plate LED power source according to an embodiment of the present invention.

A lower plate LED power source 113 and a far-infrared heating element 116 are disposed on the lower plate 20.

Several brackets 31 are installed on a steel plate at regular intervals to prevent the lower LED power source 113 from shaking.

FIG. 5 is a view with the heater bracket on the lower plate removed according to an embodiment of the present invention.

In the view with the heater bracket of the lower plate 20 shown in FIG. 5 removed, a ventilator 41 and a driving motor, etc. are built into the interior 40 of the lower plate 20. The sweat outlet 27 collects and discharges the user's sweat that accumulates on the bottom of the lower plate 20.

FIG. 6 is an upper plate configuration diagram according to an embodiment of the present invention.

The upper plate 10 consists of an upper LED power source unit 114, a upper UVC LED power source unit 115, and a far-infrared heating element 116, and a PC plate that can pass through light is coupled to the upper plate power source unit. A plurality of brackets 117 that serve to fix the upper plate LED power source unit 114 and the UVC LED power source unit 115 so as not to shake are arranged at regular intervals.

FIG. 7 is a configuration diagram of a far-infrared heating element disposed at the upper plate according to an embodiment of the present invention.

The upper power source consists of an upper LED power source 114, a upper UVC LED power source 115, and a far-infrared heating element 116. The upper plate 10 and the lower plate 20 are connected with two hinges. The means for opening and closing the upper plate 10 is a shock absorber 26.

The far-infrared heating element 116 according to an embodiment of the present invention uses an illite heating element with good heat generation efficiency. Illite is a representative clay mineral, which contains porous (low potassium content) biotite-based minerals and has a plate-like structure.

FIG. 8 is a block diagram of a control unit according to an embodiment of the present invention.

In the present invention, the control unit 100 consists of a power source unit 110, an operation mode control unit 120, a sensor unit 130, a timer unit 140, an alarm sound generator 150, a chamber opening/closing unit 160, and a display driving unit 170, a ventilation unit 180, an information processing unit 190, and a memory unit 200.

The display driving unit 170 can display the current time, entry time into the chamber, and remaining time on a display device such as an LCD.

The timer unit 140 checks the power source time for far infrared rays and near infrared rays.

The alarm sound generator 150 generates an alarm sound when the core body temperature is 40° C. or higher.

The sensor unit 130 detects temperature, humidity and human body within the chamber.

FIG. 9 is a configuration diagram of a power source unit according to an embodiment of the present invention.

The power source unit 110 consists of a chamber power source unit 112, a lower plate LED power source unit 113, an upper plate LED power source unit 114, an upper plate UVC LED power source unit 115, and a far-infrared heating element 116.

In the description of the present invention, the power source of the lower plate consists of a chamber power source unit 112, a lower plate LED power source unit 113, and a far-infrared heating element 116.

The power source of the upper plate consists of an upper plate LED power source unit 114, a upper plate UVC LED power source unit 115 and a far-infrared heating element 116.

The power is 120V/220V, 50~60 Hz. The direct currents converted by the AC/DC converter is 12V, 24V, and 48V. The 12V is supplied to the lower plate LED power source unit 113 and the upper LED power source unit 114. 24V direct current electricity is used to drive shock absorber, motor, or other equipments.

48V is used in the upper UVC LED power source unit 115.

Using direct current (DC) as a power prevents electromagnetic waves from being generated.

Since the user lies down in the chamber and stays there for 1 hour, there must be no electromagnetic waves.

In one embodiment of the present invention, power consumption is 2.5 Kw.

When preheating, it is 1, 5 Kw max, and when operating, it is 2.0 Kw max.

FIG. 10 is a configuration diagram of a sensor unit according to an embodiment of the present invention.

The sensor unit 130 consists of a temperature sensor 131, a humidity sensor 132 and a human body detection sensor 133.

Three temperature sensors 131 are installed spaced apart from each other at regular intervals on the bottom of the lower plate where the user lies, and two are attached to the upper plate. The humidity sensor 132 and the human body detection sensor 133 are attached to the upper plate. The humidity sensor 132 is a sensor that detects humidity inside the chamber.

The human body detection sensor 133 is a sensor that detects whether a user is inside the chamber.

Since ultraviolet rays generated from the UVC LED power source unit 115 are harmful to the human body, the human body detection sensor 133 turns off the UVC LED power source unit 115 when a user is present.

Method for Measuring Core Body Temperature

1. Core body temperature refers to the temperature inside the body. The core body temperature of the human body is around 37° C., the average temperature is 34-35° C. on the skin surface, and in the peripheral parts of the extremities, the temperature may drop considerably below the environmental temperature. The body temperature of healthy adults is around 36.5° C., but the body temperature is slightly lower in the elderly and slightly higher in infants (Source: Asan Medical Center, Seoul).

2. Core body temperature refers to the temperature of internal organs of the body, such as the heart or bladder, which is distinct from the peripheral part temperature of the extremities. Because the anesthesia administered during surgery may inhibit the ability to regulate the core body temperature, it is desirable to repeatedly check the core body temperature. Core body temperature can be measured with the US 3M™ Bair Hugger Control Unit.

3. In the present invention, core body temperature refers to the body temperature of the user's head, chest and abdomen. In order to monitor and maintain the core body temperature in various clinical settings, an accurate measurement method focusing on non-invasive way is needed. The Tcore temperature monitoring system developed by German company Dräger is a safe and accurate non-invasive way. In one embodiment of the present invention, the Tcore temperature monitor can be attached to the user's forehead and measure the core body temperature.

4. By using the gSKIN® CBT sensor developed by GreenTEG in Switzerland, it is possible to accurately measure the core temperature on the skin without penetrating into the body. The gSKIN® CBT sensor is ultra-small at 2 mm×2 mm, can be easily applied to watch-type wearable devices, and can measure the core temperature in real time without significant impact on daily life.

5. In one embodiment of the present invention, after turning ON the power of the lower plate LED power source unit 113 and the upper plate LED power source unit 114, the surface temperature of the PC board, the temperature at the bottom of the PC board and the temperature inside the chamber were measured through a temperature sensor installed inside the chamber over time (minutes).

The core body temperature was calculated and determined using the following calculation formula that may calculate the core body temperature using the measured temperature data. TB represents the core body temperature, and T1, T2, and T3 represent the PC board surface temperature, the PC board bottom temperature, and chamber internal temperature in the chamber shown in FIG. 2, respectively.

The user's core body temperature TB is calculated and measured based on the condition values described above under the following assumptions.

Assumption 1: Heat flows only in the vertical direction and thermal conditions in the measurement area are assumed to be constant.

Assumption 2: Looking at Fourier's law of heat conduction from an electrical perspective, the thermal conductivity, thickness and area of the heat-conducting material are considered resistance to heat flow.

Therefore, Fourier's heat conduction equation can be expressed as Equation 1 as follows.

$$q = \frac{\Delta T}{\frac{x}{kA}} = \frac{\Delta T}{R_{th}} \quad \text{Equation 1}$$

The PC board surface temperature T1, PC board bottom temperature T2, and chamber internal temperature T3 are measured as shown in Table 1. It can be expressed as the following equations 2 and 3.

$$q_{left} = \frac{T_B - T_1}{R_s} = \frac{T_1 - T_2}{R_1} = \frac{T_2 - T_A}{R_A} \quad \text{Equation 2}$$

$$q_{right} = \frac{T_B - T_3}{R_s + R_2} = \frac{T_3 - T_A}{R_A} \quad \text{Equation 3}$$

Here, the meanings of the condition values TB, T1, T2, and T3 are as described above.

Therefore, by solving the simultaneous equations of Equation 2 and Equation 3, Equation 4 and Equation 5, which determine the core body temperature TB using the condition values T1, T2, T3, and TA, are as follows.

$$T_B = T_3 + \frac{(T_1 - T_2)(T_3 - T_A)}{K(T_2 - T_A)} \quad \text{Equation 4}$$

$$K = \frac{R1}{R_2 + R_S} \quad \text{Equation 5}$$

The core body temperature is calculated and measured using the above-mentioned equations using the K value which is the temperature estimation correction coefficient.

Experimental Example 1

The results of measuring the PC board surface temperature T1, PC board lower temperature T2, and chamber internal temperature T3 using three temperature sensors according to Experimental Example 1 of the present invention are shown in Table 1 below.

TABLE 1

Core body temperature measurement data by LED infrared irradiator (Unit: ° C.)

| Elapsed time (minutes) | PC board surface temperature (T1) | PC board bottom temperature (T2) | Chamber internal temperature (T3) | Core body temperature (TB) |
|---|---|---|---|---|
| 5 | 48.5 | 28.6 | 24.5 | 36.8 |
| 10 | 60.6 | 37.5 | 27.5 | 38.7 |
| 15 | 78.3 | 56.9 | 38.1 | 39.5 |
| 20 | 65.6 | 46.4 | 38.2 | 40.5 |
| 30 | 70.2 | 49.6 | 37.9 | 41.5 |
| 35 | 74.5 | 52.1 | 37.6 | 40.8 |
| 40 | 73.8 | 51.9 | 37.4 | 41.4 |

FIG. 11 is a configuration diagram of an LED unit according to an embodiment of the present invention.

According to an embodiment of the present invention, the lower plate LED power source unit and the upper plate LED power source unit combine LED units. An LED unit refers to an arrangement of multiple LED chips in a long frame.

There are four types of LEDs used in one embodiment of the present invention: 600 nm visible light LED and near-infrared LED that generate light with wavelengths of 810 nm, 940 nm, and 1,200 nm.

In FIG. 11 (*a*), one LED unit is arranged by mixing 600 nm visible light LED (a), 810 nm LED (b), 940 nm LED (c), and 1,200 nm LED (d), and three rows of LED units are arranged in parallel. This is a drawing showing the arrangement. Here, the 600 nm visible light LED (a) is provided because the light can be seen. Since the 810 nm LED (b), 940 nm LED (c), and 1,200 nm LED (d) cannot see the light generated, the 600 nm visible light LED (a) is placed so that the user can feel the light, 600 nm visible light LED light is a light that is not harmful to the eyes.

Visible light ray is the light that can be seen with the eyes, and its wavelength is 380 to 780 nm.

FIG. 11 (*b*) shows multiple 600 nm visible light LEDs (a) arranged in one LED unit, Additionally, multiple 810 nm LEDs (b) are arranged in one LED unit; 940 nm LED (c)) is arranged in another LED unit; In addition, 1,200 nm LED(d) is arranged in one LED unit. Here, the 600 nm visible light ray LED (a) is placed because the light can be seen.

FIG. 11 (b) shows that multiple 600 nm visible light LEDs (a) are arranged in one LED unit, multiple 810 nm LEDs (b) are arranged in another LED unit, 940 nm LED (c)) is arranged in another LED unit, and 1, 200 nm LED (d) is arranged in another LED unit. Here, the 600 nm visible light LED (a) is placed because the light can be seen.

FIG. 12 is a diagram showing a combination of LEDs in multiple wavelength bands.

The LEDs shown in FIG. 12 are 810 nm LED (a), 940 nm LED (b), 1,200 nm LED (c) and 600 nm visible light ray LED (d). Here, the 600 nm visible light ray LED (a) is placed because the light can be seen. FIG. 12 (a) shows a case where the four LEDs are mixed and each far-infrared ray is stack-combined on the heating element (e) and arranged in a plate.

FIG. 12 (b) shows a case where 810 nm LED (a), 940 nm LED (b), 1,200 nm LED (c) and 600 nm visible light ray LED (d) are stack-combined and arranged on a far-infrared ray heating element (e).

FIG. 13 is a diagram of a combination of a near-infrared ray LED and a far-infrared ray heating element.

FIG. 13 shows a case where three LEDs and three far-infrared ray heating elements (e) (e) are arranged in combination.

FIG. 14 is a configuration diagram of the LED power source unit on the lower plate.

The power source 50 on the lower plate converts AC 120V/220V into 12V direct current using the AC/DC converter 51. Subsequently, 12V power is supplied to the A-type LED unit (52) and B-type LED unit (53) through a resistor. The A-type LED unit 52 has multiple 600 nm visible light LEDs arranged.

The B-type LED unit 53 is disposed by mixing 810 nm LED, 940 nm LED and 1, 200 nm LED. Five to ten A-type LED units and five to ten B-type LED units are placed on the lower plate 20. In the best embodiment, nine A-type LED units and nine B-type LED units are preferably installed on the lower plate 20.

One embodiment of the present invention can control nine A-type LED units and nine B-type LED units, respectively. Further, a resistor is installed on each line and therefore, it is possible to figure out the power supplied to each A-type LED unit 52 and each B-type LED unit 53.

The lifespan of the LED chip can be predicted through changes in the power supplied to each A-type LED unit 52 and each B-type LED unit 53, and can be easily replaced in case of failure.

That is, according to the present invention, each A-type LED unit 52 and each B-type LED unit 53 can control power separately, and therefore, there is an advantage in that each LED unit A/S can be performed.

FIG. 15 is a configuration diagram of the LED power unit in the upper plate.

The power source 50 of the upper plate converts AAC 120V/220V into 12V direct current using the AC/DC converter 51. Subsequently, 12V power is supplied to the A-type LED unit 52, B-type LED unit 53 and ultraviolet UVC LED 54, through a resistor. The A-type LED unit 52 has several 600 nm visible light LEDs arranged therein.

The B-type LED unit 53 is disposed by mixing 810 nm LED, 940 nm LED and 1, 200 nm LED. And, two ultraviolet UVC LEDs 54 are provided.

The ultraviolet UVC LED (54) has a wavelength of 275 nm and a view angle of 120°. The power supplied to the ultraviolet UVC LED (54) is 48V.

Four to eight A-type LED units and four to eight B-type LED units are placed on the upper plate (10). In the best embodiment, eight A-type LED units and eight B-type LED units are preferably installed on the lower plate 20.

The lifespan of the LED chip can be predicted by changing the power supplied to each type LED unit 52 and each B-type LED unit 53, and if the LED chip breaks down, it can be easily replaced.

That is, according to the present invention, each A-type LED unit 52 and each B-type LED unit 53 can control the power separately and therefor, there is an advantage that after-sales service can be performed for each LED units.

FIG. 16 is a flow diagram of the operation of the LED infrared ray irradiator according to the present invention.

The operation of the LED infrared irradiator according to one embodiment of the present invention proceeds in the following order.

After turning on the chamber power (S10), the far-infrared heating element (S20) is turned on. It is determined whether the temperature is above 36° C. and the humidity is below 50% inside the chamber (S30).

If the temperature is not above 36° C. or the humidity is not below 50%, the far-infrared heating element power is continuously kept ON (S20). If the temperature is above 36° C. and the humidity is below 50%, the far-infrared heating element is turned off (S40).

Next, the near-infrared LED power is turned on (S50). Thereafter, it is determined whether the core body temperature is above 40° C. (S60). If the core body temperature is not above 40° C., it is determined whether the set time has elapsed (S61). If the set time has not elapsed, the near-infrared LED power is kept ON (S50). If the set time has elapsed, the near-infrared LED power is turned off (S62) and the chamber power is turned off (S80).

If the core body temperature is above 40° C., the near-infrared LED power is turned off (S70), and then it is determined whether the set time has elapsed (S71). If the set time has not elapsed, it is determined whether the core body temperature is above 40° C. (S60). If the set time has passed, the chamber power is turned off (S80).

FIG. 17 is a flowchart showing a method for disinfecting the inside of a chamber of the present invention.

The method of disinfecting the inside of the chamber according to an embodiment of the present invention proceeds in the following order. According to the flowchart shown in FIG. 17, the chamber power is firstly turned on (S100). Thereafter, the far-infrared heating element power is turned on (S110), and it is determined whether the set time has elapsed (S120). If the set time has not elapsed, the far-infrared heating element power is kept ON (S110). If the set time has elapsed, the far-infrared LED power is turned off (S130).

Then, the ultraviolet UVC LED power is turned on (S140). Depending on whether the set time has elapsed (S150), if the set time has not elapsed, the ultraviolet UVC LED power is kept ON, and if the set time has elapsed, the ultraviolet UVC LED power is turned off (S160). Then, the chamber power is turned off (S170).

FIG. 18 is a structural diagram of the actuator installed on the upper plate.

In another embodiment of the present invention, the actuator is installed outside the upper plate 10.

The upper part of the actuator 300 shown in FIG. 18 is coupled to a first fixing part 310 attached to the upper plate 10, and the lower part of the actuator 300 is coupled to a second fixing part 320 attached to the lower plate 20.

One or two more hinges 330 are installed to couple the upper plate 10 and the lower plate 20 and support the upper plate 10 so that it can move up and down.

FIG. 19 is a diagram showing that the upper plate is opened by the operation of the actuator.

When the chamber opening/closing unit 160 in the control unit 100 instructs to open the upper plate 10, the actuator 300 operates to open the upper plate 10. Conversely, when the chamber opening/closing unit 160 instructs to close the upper plate 10, the actuator 300 operates to close the upper plate 10.

In the present invention, using of the actuator 300 as a means for opening and closing the upper plate 10 is intended to reduce noise generated in the process of opening and closing the upper plate 10 and promote user's safety.

Experimental Example 2

The experimental Example 2 is the results of identifying the waste (sweat) discharge characteristics of users of the LED infrared irradiator according to the present invention in which the patient's sweat discharged using the LED infrared irradiator of the present invention has been analyzed.

In experimental Example 2, tables 2 and 3 below show the results of a study on the characteristics of waste discharge according to infrared ray irradiation by the LED infrared ray irradiator targeting cancer patients among users.

TABLE 2

| No. | Gender | Ages |
|---|---|---|
| 1 | F | 58 |
| 2 | M | 41 |
| 3 | F | 64 |
| 4 | F | 58 |
| 5 | F | 26 |
| 6 | M | 50 |
| 7 | F | 52 |
| 8 | F | 26 |
| 9 | F | 54 |
| 10 | F | 49 |
| 11 | F | 61 |
| 12 | M | 56 |
| 13 | F | 41 |
| 14 | M | 63 |
| 15 | M | 41 |
| 16 | F | 42 |
| 17 | E | 34 |
| 18 | F | 30 |
| 19 | F | 28 |
| 20 | F | 64 |
| 21 | F | 27 |
| 22 | M | 67 |
| 23 | M | 67 |

TABLE 3

| TOXIC ELEMENTS | | | | | | |
|---|---|---|---|---|---|---|
| 1 | 2 | 3 | 4 | 5 | 6 | 7 |
| Al | As | Be | Cd | Ni | Pb | Tl |

| NUTRIONAL ELEMENTS | | | | | | | | | |
|---|---|---|---|---|---|---|---|---|---|
| 1 | 2 | 3 | 4 | 5 | 6 | 7 | 8 | 9 | 10 |
| Ca | Co | Cr | Cu | Fe | Mg | Mn | Se | V | Zn |

The main results are that the concentrations of Be, Ni and Ti among toxic heavy metals (Al, As, Be, Cd, Ni, Pb, Tl) in the users' heat treatment waste (sweat) have exceeded the standard values.

Some users have confirmed that Al, Ni and Pb are discharged at high concentrations. In the case of nutrients, Ca, Fe, and Mg have been discharged at high concentrations from heat treatment waste (sweat).

The LED infrared ray irradiator of the present invention can quickly heat the chamber with far-infrared rays, reduce the time when the user spends in the chamber, improve the turnover rate of the chamber and provide a near-infrared wavelength that penetrates deepest into the human skin and increases temperature among near-infrared wavelengths, therefore, the present invention is usefully applicable in the medical industry.

The invention claimed is:

1. An LED infrared irradiator comprising an upper plate, a lower plate having a space for a user to lie down, a poly carbonate (PC) board disposed on an upper surface of the lower plate and having a size that can accommodate an entire body of the user, a handle part, a head part, a cover part, an oxygen generator, and a control unit attached to an upper side of the upper plate, wherein a power source of the lower plate comprises a chamber power source unit, a lower plate LED power source unit and a far-infrared heating element, and a power source of the upper plate comprises an upper plate LED power source, an upper plate UVC LED power source, and a far-infrared heating element, and wherein a material of the upper and lower plates is ABS resin, and each of the upper and lower plates comprises double walls being characterized in that:
    an eco-friendly foamed graphite insulation material is built in between the double walls;
    the lower plate includes a bracket, a lower body part, a pillow for placing the user's head, a storage stand for placing a water cup, a mobile phone storage stand, a shock absorber, a sweat outlet, a hinge, a moving wheel, and a space into which an injection line that supplies the fluid can enter when the user receives an IV injection;
    the control unit includes a control power source unit, an operating mode control unit, a sensor unit, a timer unit, an alarm sound generator, a chamber opening/closing unit, a display driving unit, and a ventilation unit, an information processing unit, and a memory unit;
    the control power source unit includes the chamber power source unit, the lower plate LED power source unit, the upper plate LED power source unit, the upper UVC LED power source unit, and the far-infrared heating element;
    wherein the far infrared heating element is operative to quickly heat the chamber with far-infrared rays relative to the upper and lower plate LED power sources;
    the sensor unit includes a temperature sensor, a humidity sensor, and a human body detection sensor for detecting whether a user is inside the chamber;
    the lower LED power source unit consists of comprises an A-type LED unit in which several nm visible light LEDs are arranged, and a B-type LED unit in which 810 nm LEDs, 940 nm LEDs, and 1,200 nm LEDs are mixed and arranged to intensively increase a core body temperature of the user with near-infrared ray wavelengths that penetrate more than 5 mm into a humans skin and increase the temperature of the skin to help prevent diseases and pains and block convective heat generated from the LEDs allowing users to receive infrared ray irradiation all over their body;
    the lower plate LED power source unit converts AC 120-220V into 12V direct current using an AC/DC converter and supplies it, and controls the power of the A-type LED unit and the B-type LED unit, respectively;
    the upper plate LED power source unit comprises an A-type LED unit in which several 600 nm visible light LEDs are arranged, a B-type LED unit in which 810 nm LEDs, 940 nm LEDs and 1,200 nm LEDs are mixed and arranged and an ultraviolet UVC LED, wherein a number of the A-type LED units is 4 to 8, a number of the B-type LED units is 4 to 8, and a number of the ultraviolet UVC LEDs is 2 to 3; and the lower upper plate LED power source unit converts AC 120/220V into 12V direct current to prevent electromagnetic waves from being generated using the AC/DC converter to supply power to the A-type LED unit and B-type LED unit, respectively and converts AC 120/220V into 48V direct current using an AC/DC converter, supplies it to two ultraviolet LEDs and controls them respectively; and wherein the temperature sensor is provided inside the chamber, wherein the temperature sensor is operative to measure the PC board surface temperature, the PC board bottom temperature, and the chamber internal temperature in the chamber, wherein the core body temperature is calculated using the PC board surface temperature, the PC board bottom temperature, and chamber internal temperature in the chamber.

2. The LED infrared irradiator of claim 1, wherein the sweat outlet is located on a bottom of the lower plate, wherein the sweat outlet is configured to collect and discharge sweat of the user that accumulates on the bottom of the lower plate.

3. The LED infrared irradiator of claim 1, wherein the far infrared heating element comprises an illite heating element for improving blood circulation, activating cells, strengthening immunity, providing deep penetration heat into the body, antibacterial and deodorize, and reduce cancer cell proliferation.

4. The LED infrared irradiator of claim 1, wherein the core body temperature was calculated using the following formula:

$$T_B = T_3 + \frac{(T_1 - T_2)(T_3 - T_A)}{K(T_2 - T_A)}$$

where $T_B$ represents the core body temperature, K is the temperature estimation correction coefficient, and $T_1$, $T_2$, and $T_3$ represent the PC board surface temperature, the PC board bottom temperature, and chamber internal temperature in the chamber, respectively.

5. The LED infrared irradiator of claim 1, wherein the far-infrared heating element is operative to be powered on in response to the temperature sensor detecting a temperature inside the chamber that is not above a first predetermined temperature and the humidity sensor detecting a humidity of the chamber that is not below a predetermined humidity, wherein the far-infrared heating element is operative to be powered off in response to the temperature sensor detecting a temperature inside the chamber that is above the first predetermined temperature and the humidity sensor detecting a humidity of the chamber that is below a predetermined humidity.

6. The LED infrared irradiator of claim 1, wherein the upper plate LED power source unit and the lower plate LED power source unit are powered on when the temperature sensor detects a core body temperature to be not above a second predetermined temperature and a predetermined set time unit has not elapsed, wherein the upper plate LED power source unit and the lower plate LED power source unit are powered off when the temperature sensor detects a core body temperature to be above the second predetermined temperature and the set time has elapsed.

7. The LED infrared irradiator of claim 6, wherein the far-infrared heating element is operative to be powered on in response to the temperature sensor detecting a temperature inside the chamber that is not above a first predetermined temperature and the humidity sensor detecting a humidity of the chamber that is not below a predetermined humidity, wherein the far-infrared heating element is operative to be powered off in response to the temperature sensor detecting a temperature inside the chamber that is above the first predetermined temperature and the humidity sensor detecting a humidity of the chamber that is below a predetermined humidity.

8. The LED infrared irradiator of claim 1, wherein the far-infrared heating element is operative to be powered on and kept on until a predetermined set time has elapsed.

9. The LED infrared irradiator of claim 1, wherein the UVC LED power source unit is operative to be powered on and kept on until a predetermined set time has elapsed.

10. The LED infrared irradiator of claim 1 further comprising three rows of lower LED power source units arranged in parallel, wherein the 600 nm visible light LED is placed so that the user can feel the light.

11. The LED infrared irradiator of claim 1, wherein the LEDs are stack-combined and arranged on the far-infrared heating element.

12. The LED infrared irradiator of claim 1, wherein three LEDs and three far-infrared ray heating elements are arranged in combination.

13. An LED infrared irradiator comprising an upper plate, a lower plate having a space for a user to lie down, a poly carbonate (PC) board disposed on an upper surface of the lower plate and having a size that can accommodate an entire body of the user, a handle part, a head part, a cover part, an oxygen generator, and a control unit attached to an upper side of the upper plate, wherein a power source of the lower plate comprises a chamber power source unit, a lower plate LED power source unit and a far-infrared heating element, and a power source of the upper plate comprises an upper plate LED power source, an upper plate UVC LED power source, and a far-infrared heating element, and wherein a material of the upper and lower plates is ABS resin, and each of the upper and lower plates comprises double walls being characterized in that:

an eco-friendly foamed graphite insulation material is built in between the double walls;

wherein the far infrared heating element is operative to quickly heat the chamber with far-infrared rays relative to the upper and lower plate LED power sources;

the lower LED power source unit comprises an A-type LED unit in which several nm visible light LEDs are arranged, and a B-type LED unit in which 810 nm LEDs, 940 nm LEDs, and 1,200 nm LEDs are mixed and arranged to intensively increase a core body temperature of the user with near-infrared ray wavelengths that penetrate into the human skin and increase the temperature of the skin to help prevent diseases and pains and block convective heat generated from the LEDs allowing users to receive infrared ray irradiation all over their body;

the lower plate LED power source unit converts AC 120-220V into 12V direct current using an AC/DC converter and supplies it, and controls the power of the A-type LED unit and the B-type LED unit, respectively;

the upper plate LED power source unit comprises an A-type LED unit in which several 600 nm visible light LEDs are arranged, a B-type LED unit in which 810 nm LEDs, 940 nm LEDs and 1,200 nm LEDs are mixed and arranged and an ultraviolet UVC LED;

and the upper plate LED power source unit converts AC 120/220V into 12V direct current to prevent electromagnetic waves from being generated using the AC/DC converter to supply power to the A-type LED unit and B-type LED unit, respectively and converts AC 120/220V into 48V direct current using an AC/DC converter, supplies it to two ultraviolet LEDs and controls them respectively; the LED infrared irradiator further comprising a temperature sensor, a humidity sensor, and a human body detection sensor for detecting whether a user is inside the chamber, wherein the far-infrared heating element is operative to be powered on in response to a temperature sensor detecting a temperature inside the chamber that is not above a first predetermined temperature and the humidity sensor detecting a humidity of the chamber that is not below a predetermined humidity, wherein the far-infrared heating element is operative to be powered off in response to the temperature sensor detecting a temperature inside the chamber that is above the first predetermined temperature and the humidity sensor detecting a humidity of the chamber that is below a predetermined humidity; wherein the temperature sensor is provided inside the chamber, wherein the temperature sensor is operative to measure the PC board surface temperature, the PC board bottom temperature, and the chamber internal temperature in the chamber, wherein the core body temperature is calculated using the PC board surface temperature, the PC board bottom temperature, and chamber internal temperature in the chamber.

14. The LED infrared irradiator of claim 13 further comprising a temperature sensor, a humidity sensor, and a human body detection sensor for detecting whether a user is inside the chamber, wherein the upper plate LED power source unit and the lower plate LED power source unit are powered on when the temperature sensor detects a core body temperature to be not above a second predetermined temperature and a predetermined set time has not elapsed, wherein the upper plate LED power source unit and the lower plate LED power source unit are powered off when the temperature sensor detects a core body temperature to be above the second predetermined temperature and the predetermined set time has elapsed.

15. The LED infrared irradiator of claim 14, wherein the far-infrared heating element is operative to be powered on in response to the temperature sensor detecting a temperature inside the chamber that is not above a first predetermined temperature and the humidity sensor detecting a humidity of the chamber that is not below a predetermined humidity, wherein the far-infrared heating element is operative to be powered off in response to the temperature sensor detecting a temperature inside the chamber that is above the first predetermined temperature and the humidity sensor detecting a humidity of the chamber that is below a predetermined humidity.

* * * * *